United States Patent [19]

Keep

[11] Patent Number: Plant 6,597

[45] Date of Patent: Feb. 14, 1989

[54] RASPBERRY PLANT — AUTUMN BLISS CULTIVAR

[75] Inventor: Elizabeth Keep, Maidstone, England

[73] Assignee: National Seed Development Organisation, Cambridge, England

[21] Appl. No.: 94,898

[22] Filed: Sep. 10, 1987

[51] Int. Cl.[4] ..... A01H 5/00

[52] U.S. Cl. ..... Plt./46

[58] Field of Search ..... Plt. 46

*Primary Examiner*—James R. Feyrer

*Attorney, Agent, or Firm*—Burns, Doane, Swecker & Mathis

[57] ABSTRACT

This cultivar was formed by crossing two unnamed hybrid raspberry seedlings bred at the East Malling Research Station, Maidstone, Kent, England. The new cultivar is a primocane-fruiting variety wherein the fruit ripens earlier than the Heritage and September varieties. The resulting fruit is highly attractive, oval-conical in configuration, and medium to dark red in coloration as illustrated.

2 Drawing Sheets

SUMMARY OF THE INVENTION

The original plant of the new cultivar was selected from a family of seedlings resulting from a cross made in 1973 at the East Malling Research Station (now the Institute of Horticultural Research) of the Kent Incorporated Society for Promoting Experiments in Horticulture, East Malling, Maidstone, Kent, England. Each parent was a complex hybrid produced at the East Malling Research Station. The maternal parent was derived from *Rubus arcticus, R. occidentalis,* and the raspberry varieties Lloyd George, Norfolk Giant, Pynes Royal, Malling Landmark, Malling Promise and Burnetholm. The male parent was derived from a *R. idaeus* strigosus selection.

The performance of the new cultivar has been evaluated at the East Malling Research Station; the National Fruit Trials at Faversham, Kent, England; and elsewhere in the United Kingdom and Europe. The characteristics of the new cultivar have been found to be stable and have been transmitted without change through succeeding asexual propagations. The new cultivar may be propagated through the use of suckers produced in a spawn-bed, from root cuttings, and by use of tissue culture techniques.

The new cultivar has been named Autumn Bliss.

BRIEF DESCRIPTION OF THE PHOTOGRAPHS

The accompanying photographs show typical specimens of the new cultivar in color as true as reasonably possible to make the same in color illustrations of this character. In each instance the photographs were taken at the East Malling Research Station, Maidstone, Kent, England.

Figure 1:
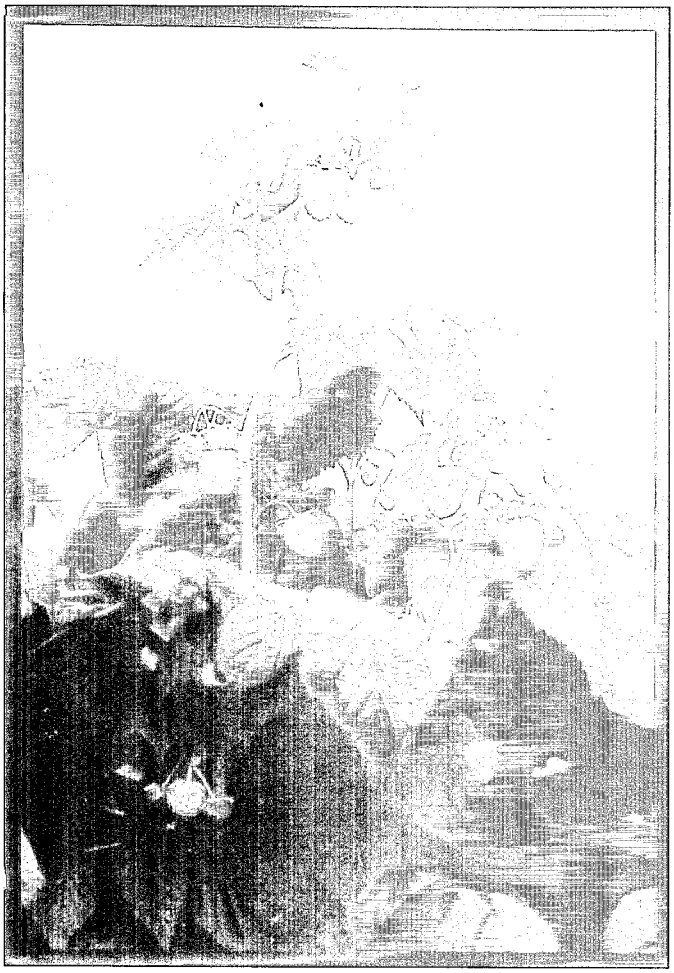
FIG. 1 is a view of two primocane tips showing a typical distribution of fruit, the fruit size and shape, and the leaf morphology.
Figure 2:
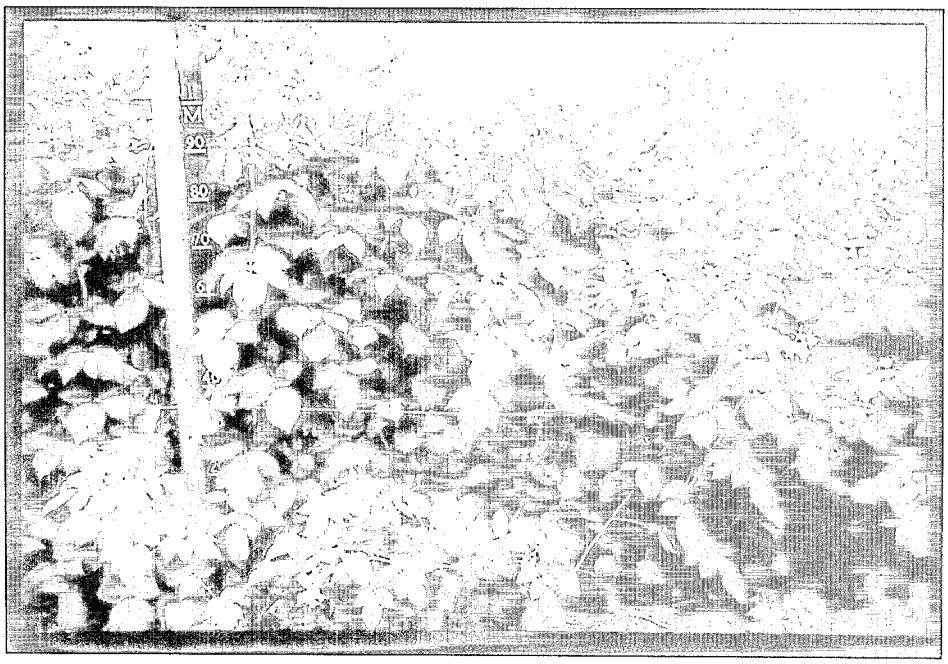
FIG. 2 is a view of a section of a fruiting row during mid-August showing both the ripe and immature fruit borne at the tips of primocanes, wherein the primocanes commonly have a height of approximately 1.0 to 1.25 meters.
Figure 3:
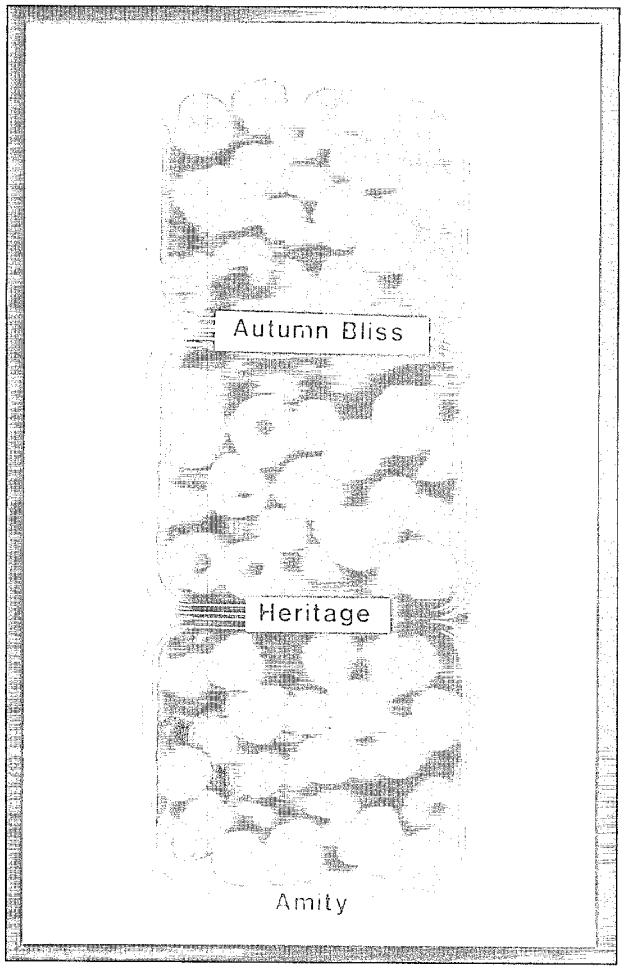

FIG. 3 is a top view for comparative purposes of punnets containing the fruit of the Autumn Bliss, Heritage and Amity cultivars. The fruit of Autumn Bliss is generally darker and larger than that of Heritage. The fruit of Autumn Bliss also commonly is brighter and more conical than that of Amity. This photograph was taken at the beginning of October, and illustrates the late season fruit of Autumn Bliss, the early-season fruit of Heritage, and the mid-season fruit of Amity. Since the fruit size generally tends to decrease throughout the ripening season for all raspberry varieties, it is inappropriate to compare fruit picked on the same day from varieties with different fruiting seasons. The mean fruit weight over two seasons for Autumn Bliss, Heritage, and Amity was found to be 3.7, 2.8 and 3.2 grams respectively.

Figure 4:
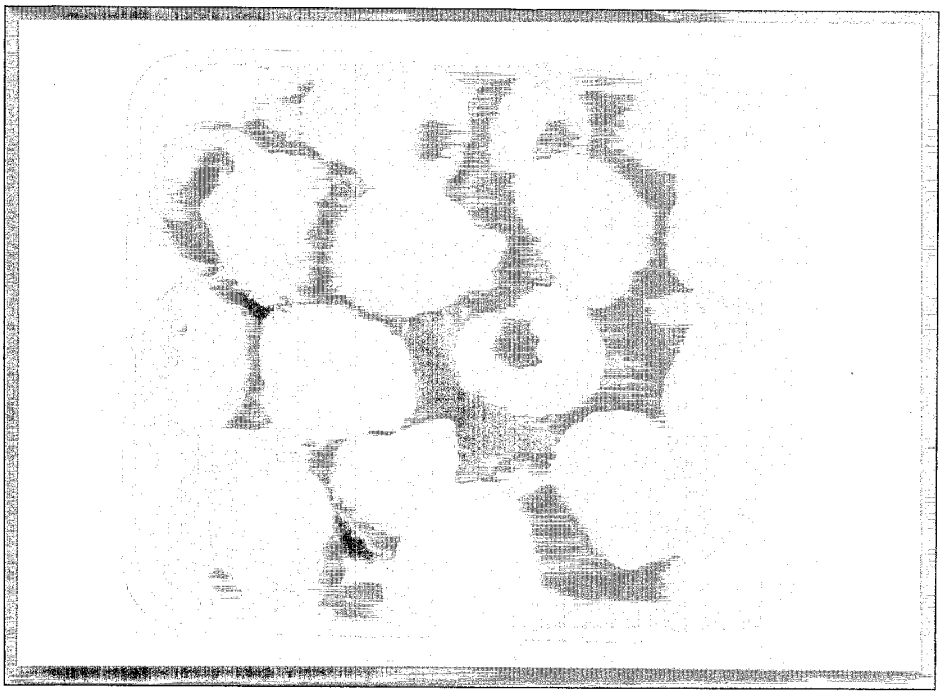

FIG. 4 is a top view of a punnet of Autumn Bliss fruit. The photograph was taken during mid-August.

DETAILED DESCRIPTION

The following is a detailed description of the characteristics of the new cultivar as observed at the East Malling Research Station and the National Fruit Trials at Faversham. Color terminology employed is to be accorded its ordinary dictionary significance. As will be apparent to those skilled in horticultural science, the fruit color varies with the stage of ripeness.

When the new cultivar is managed as a primocane-fruiting variety (i.e., only cropped once a year), the fruiting cane is pruned to ground level following fruiting. The primocane which emerges in the Spring goes on to produce fruit in the same year. Approximately 35 to 60 percent of the nodes on the primocanes produce fruit in year one. After fruiting the primocane dies back from the tip to the lowest fruiting node. If retained, the lower part of the cane will fruit during year two.

Description of Primocane

General habit: The erect canes exhibit a medium level of vigor and commonly reach a maximum height of approximately 1.5 meters. The young canes are green with very little anthocyanin coloration.

Spines: Medium sized and numerous, deeply pigmented at the base of the spine, and have a tendency to point slightly backwards.

Leaves: Medium green, fairly flat, and moderately smooth.

Hairiness: Absent.

Bloom: Weak.

Description of Fruiting Laterals, Flowers and Fruit

Fruiting laterals: Short to medium in length (e.g., approximately 50 to 250 mm. in length), and stiffly erect. The longer laterals commonly bear 8 to 12 fruits, while the shorter laterals commonly bear less than 5 fruits.

Pedicel: Long, and green with purple spines.

Flowers: Medium size, white.

Fruit: Large, oval-conical in configuration, medium to dark red, and commonly present as fairly large individual drupelets. The mean fruit weight over a season commonly is approximately 3.5 to 4.0 grams.

Fruit quality: Medium firm, slightly glossy, with pleasant fairly mild raspberry flavor.

Plug: Blunt conical. The fruit separates form the plug moderately easily.

Season of ripening: Early to Mid-August through the first frosts in late October/early November in Southern England. Ripening time overlaps with late summer-fruiting varieties such as Malling Leo in August, and is considerably earlier than that of the September and Heritage varieties. The ripening period commonly extends over a relatively long period of approximately 12 weeks.

Yield: At the National Fruit Trials held at Faversham, the fruit production on established plants of the new variety averaged 5 tons per hectare, and nearly three times the production of the Heritage and Zeva Herbsternte varieties. The new cultivar produces a small crop in the year of establishment.

Pest and disease resistance: The new cultivar carries the gene $A_{10}$ from *Rubus occidentalis* which confers resistance to the four known races of the virus vector *Amphorophora idaei.* The new cultivar is susceptible to the pollen borne raspberry bushy dwarf virus.

Storage capacity: The fresh fruit has a limited shelf life in common with all red raspberries. The fruit of the new cultivar freezes well.

I claim:

1. A new and distinct variety of primocane-fruiting raspberry plant substantially as herein shown and described together with the parts thereof.

* * * * *